US00PP32802P2

(12) United States Plant Patent

Olesen et al.

(10) Patent No.: US PP32,802 P2
(45) Date of Patent: Feb. 9, 2021

(54) *CLEMATIS VITICELLA* PLANT NAMED 'EVIPO095'

(50) Latin Name: *Clematis viticella*
Varietal Denomination: Evipo095

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,268

(22) Filed: Sep. 3, 2019

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./226, 228
See application file for complete search history.

(56) References Cited

PUBLICATIONS

Poulsen Roser website. (http://www.poulsenroser.com/assortment/clematis-collections/boulevard/mederi.aspx). (Year: 2019).*

* cited by examiner

*Primary Examiner* — Susan McCormick Ewoldt
*Assistant Examiner* — Karen M Redden

(57) ABSTRACT

A new *Clematis* plant with a compact growth habit, profuse, red-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical Classification: Genus: *Clematis*. Species: *viticella*.

Variety denomination: 'Evipo095'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo095' originated as a single seedling from the stated cross.

The new *clematis* plant may be distinguished from its female seed parent and male pollen parent by the following characteristics. The female seed parent has violet tepals while the new variety has red-purple tepals. The male seed parent has red tepals while the new variety has red-purple tepals.

The objective of the hybridization of this *clematis* plant was to create a new and distinct variety for nursery culture with unique qualities such as:

1. Uniform and abundant red-purple flowers;
2. Vigorous and compact growth, making the variety suitable for container culture; and
3. Improved disease resistance, and
4. Flowering on new growth.

This combination of qualities was lacking in *clematis* plants that were in commercial cultivation and the qualities have been substantially achieved in the new variety.

'Evipo095' was selected by Mogens N. Olesen and Raymond J. Evison in their *clematis* development program in the Channel Islands, United Kingdom in 2008. Asexual reproduction of 'Evipo095' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo095' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo095'.

Specifically illustrated in FIG. 1 of the drawings are open flower on the plant.

Figure 1:
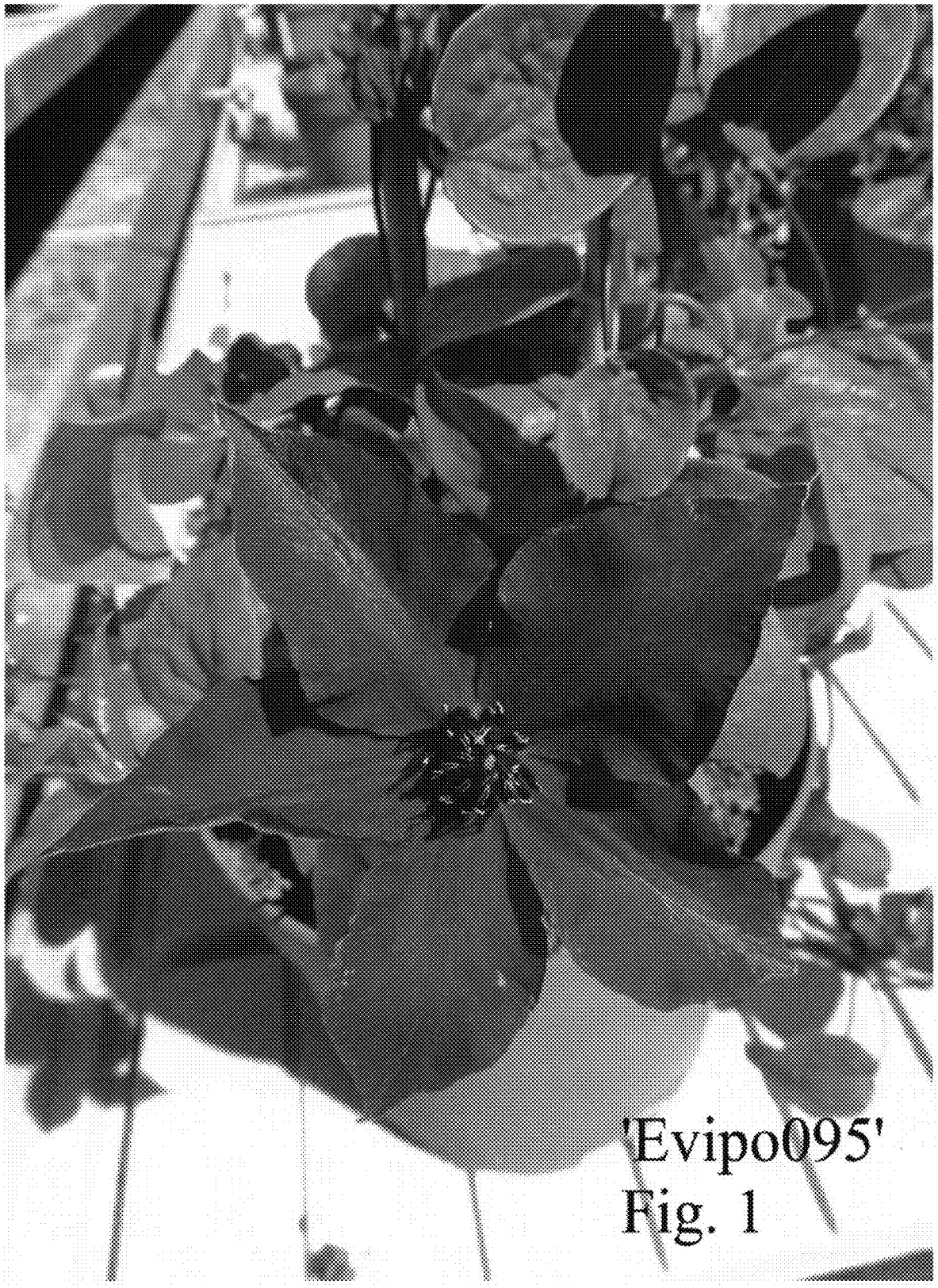
Figure 2:
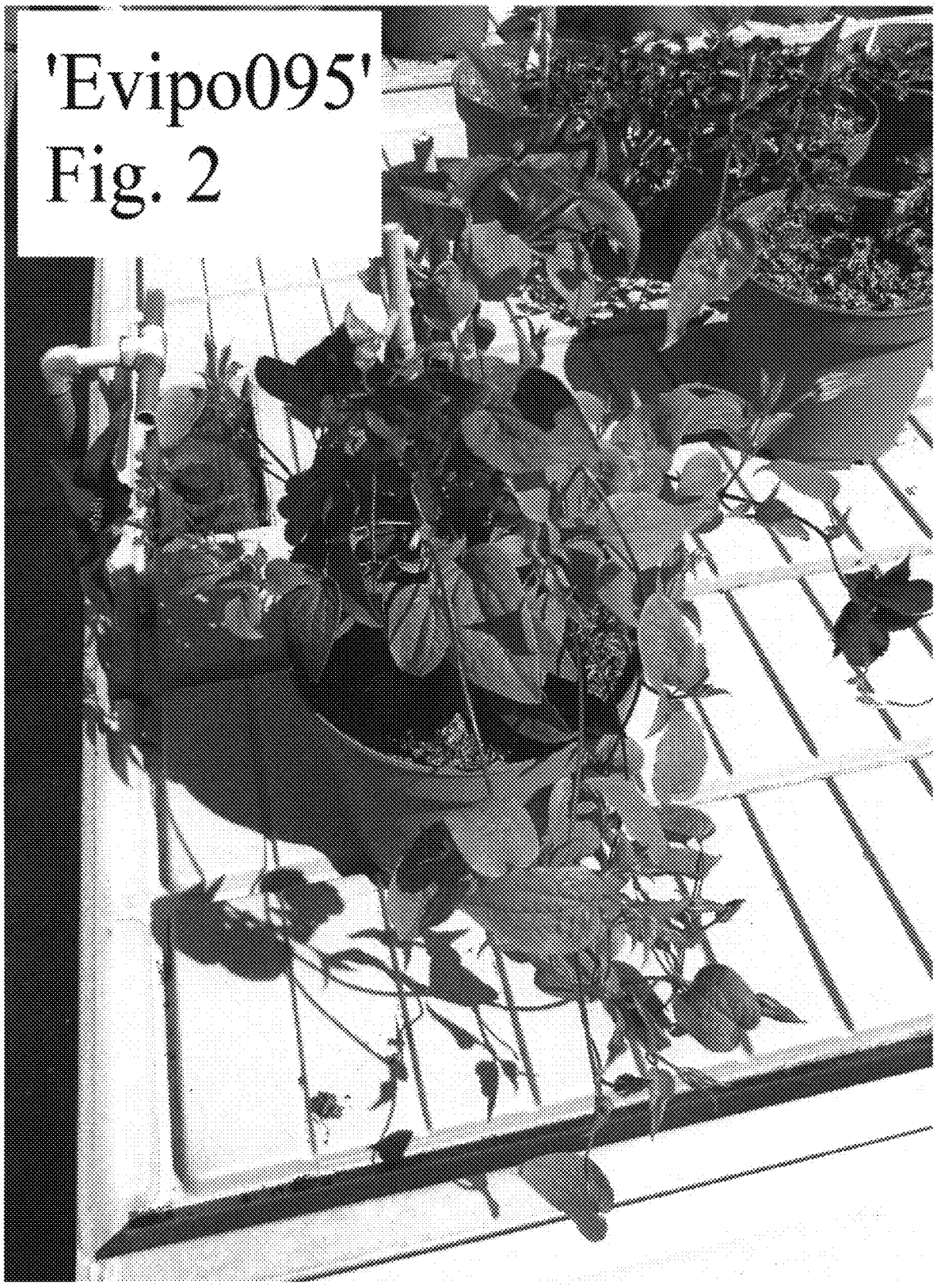
FIG. 2 shows the entire plant with open flowers.

Illustrated plants are 2 years of age.

DETAILED DESCRIPTION OF THE VARIETY

The following is a detailed description of 'Evipo095', as observed in its growth throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo070' described and illustrated in U.S. Plant Pat. No. 27,254 are compared to 'Evipo095' in Chart 1.

CHART 1

| | 'Evipo095' | 'Evipo070' |
|---|---|---|
| Flower diameter | 110 mm | 130 mm |
| Tepal upper surface after opening | Red-Purple Group 59A | Red-Purple Group 61A, 61B |
| Tepal count | 5 | 6 |

Flower and Flower Bud

Blooming habit: Continuous. The natural flowering period is generally from April to September. Flowers on new and old growth.

Flower bud:

*Size.*—Length 28 mm, diameter 14 mm.

Bud form: Elliptic.

Peduncle:

*Length.*—75 mm.

*Diameter.*—About 1 mm.

Flower arrangement:

*Borne.*—Singly.

Flower bloom:

*Size.*—Diameter 110 mm. 10 mm deep.

*Shape from the side.*—Flat.

*Fragrance.*—None.

*Lasting quality.*—Flowers normally remain 10 days on the plant.

*General tonality.*—Red-Purple Group 59A.

Tepals:

*Color.*—The upper surface is Red-Purple Group 59A. Underneath, Red Purple 59D.

*Quantity.*—Normally 5 tepals.

*Size.*—55 mm in length by 35 mm wide.

*Arrangement.*—Overlapping partially.

*Texture.*—Upper and lower surface are smooth.

Shape: Individual tepal shape is broad and elliptic. The tepal apex is acuminate. The tepal base is typically acute.

*Apex recurvature.*—Slightly recurved.

*Margins.*—Entire. Weak undulations of margin observed.

*Persistence.*—Tepals drop off cleanly.

Reproductive organs:

*Pollen.*—White Group 155 A in color.

*Anthers.*—Size: 5 mm in length. Color: Greyed-Purple Group N186A. Quantity: On average, 65.

*Filaments.*—Color: Greyed-Purple Group N186C. Length: 5 to 10 mm.

*Pistils.*—Quantity: On average, 30.

*Stigma color.*—Green-White Group 157A.

*Styles.*—Color: Green-White Group 157A. Length: 10 mm.

Plant

Size: Seasons growth attains 1.5 meters in height. About 45 cm wide.

Stems:

*Color.*—Juvenile stems are Yellow-Green Group 145B. Mature stems are Greyed-Orange Group 166B.

*Internodes.*—On average, 7 cm between nodes.

*Length.*—Normally 50 cm from the base of the plant to the flowering portion of the stem.

*Diameter.*—About 3 mm.

*Texture.*—Mature stems are ribbed. Juvenile stems are smooth.

Plant foliage:

*Arrangement.*—Ternate.

*Leaf characteristics.*—Deciduous.

*Leaf size.*—Compound leaves are 80 mm (l)×120 mm (w). Leaflets are normally 55 mm (l)×45 mm (w).

*Abundance.*—On average 2 leaves per 10 cm of stem.

Leaf color: Juvenile upper Yellow-Green Group 144A. Juvenile lower Yellow-Green Group 144A. Mature upper Yellow-Green Group 146A. Mature lower Yellow-Green Group 146B.

Leaflet shape: Generally cordate. The base is cordate to rounded, the apex is acute.

*Margin.*—Entire.

*Surface.*—The upper side is smooth. The lower side is smooth.

*Thickness.*—Moderate.

*Glossiness.*—Glossy.

Disease resistance: Subject to any disease that normally attacks the species. However the variety is more tolerant to *clematis* wilt, *Phoma clematidina*, than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo095', substantially as described and illustrated , due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo095'

'Evipo095'